United States Patent
Liu

(12)
(10) Patent No.: US 6,251,095 B1
(45) Date of Patent: Jun. 26, 2001

(54) SAFETY SYRINGE WITH RETRACTABLE STANDARD NEEDLES

(76) Inventor: Wen-Neng Liu, 19508 Nicholas Ave., Cerritos L.A., CA (US) 90701

( * ) Notice: Subject to any disclaimer, the term of this patent is extended or adjusted under 35 U.S.C. 154(b) by 0 days.

(21) Appl. No.: 09/469,370

(22) Filed: Dec. 22, 1999

(30) Foreign Application Priority Data

Dec. 15, 1999 (TW) .......................................... 87105505A01

(51) Int. Cl.$^7$ .................................................. A61M 5/315
(52) U.S. Cl. .......................................................... 604/225
(58) Field of Search .................................... 604/192–198, 604/187, 208, 218, 220, 223, 225

(56) References Cited

U.S. PATENT DOCUMENTS

| | | | |
|---|---|---|---|
| 5,485,853 | * | 1/1996 | Stubbs . |
| 5,899,887 | * | 5/1999 | Liu . |
| 5,931,813 | * | 8/1999 | Liu . |
| 5,976,108 | * | 11/1999 | Liu . |
| 6,033,385 | * | 3/2000 | Liu . |

* cited by examiner

Primary Examiner—Sharon Kennedy
Assistant Examiner—Catherine Serke
(74) Attorney, Agent, or Firm—Rosenberg, Klein & Lee

(57) ABSTRACT

Safety syringe with retractable standard needle including a syringe barrel, a plunger and an injection needle. A commonly used standard medical injection needle can be firmly fitted with the needle holder in accordance with the requirement of a user. The inner wall of the internal chamber at the open end of the syringe barrel is formed with an entrance recess extending along the axis of the internal chamber. The operating end of the plunger is formed with a radially outward projecting stopper section for preventing the needle pulling mechanism of the plunger from being accidentally latched with the needle pulling mechanism of the syringe barrel.

12 Claims, 10 Drawing Sheets

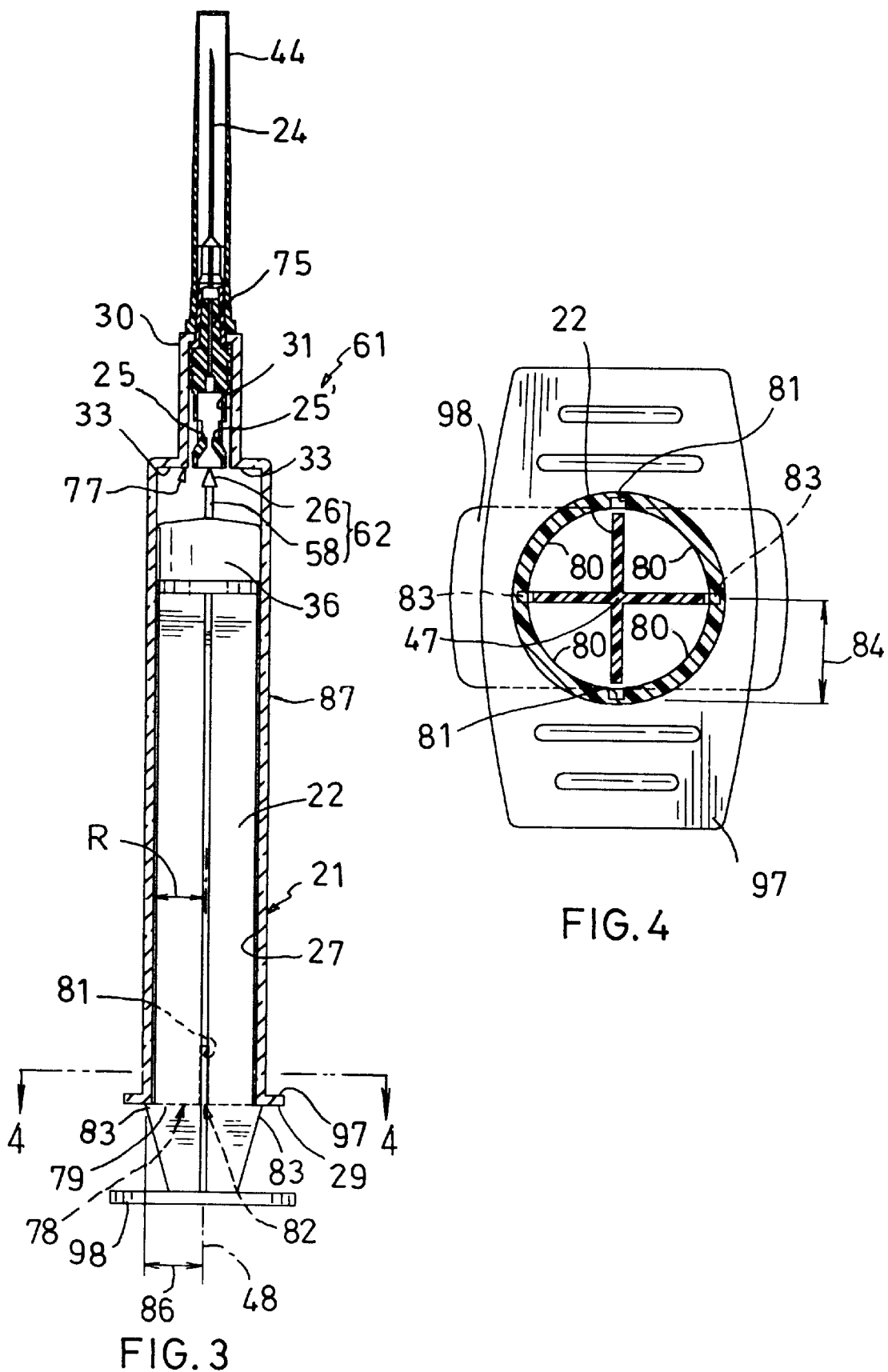

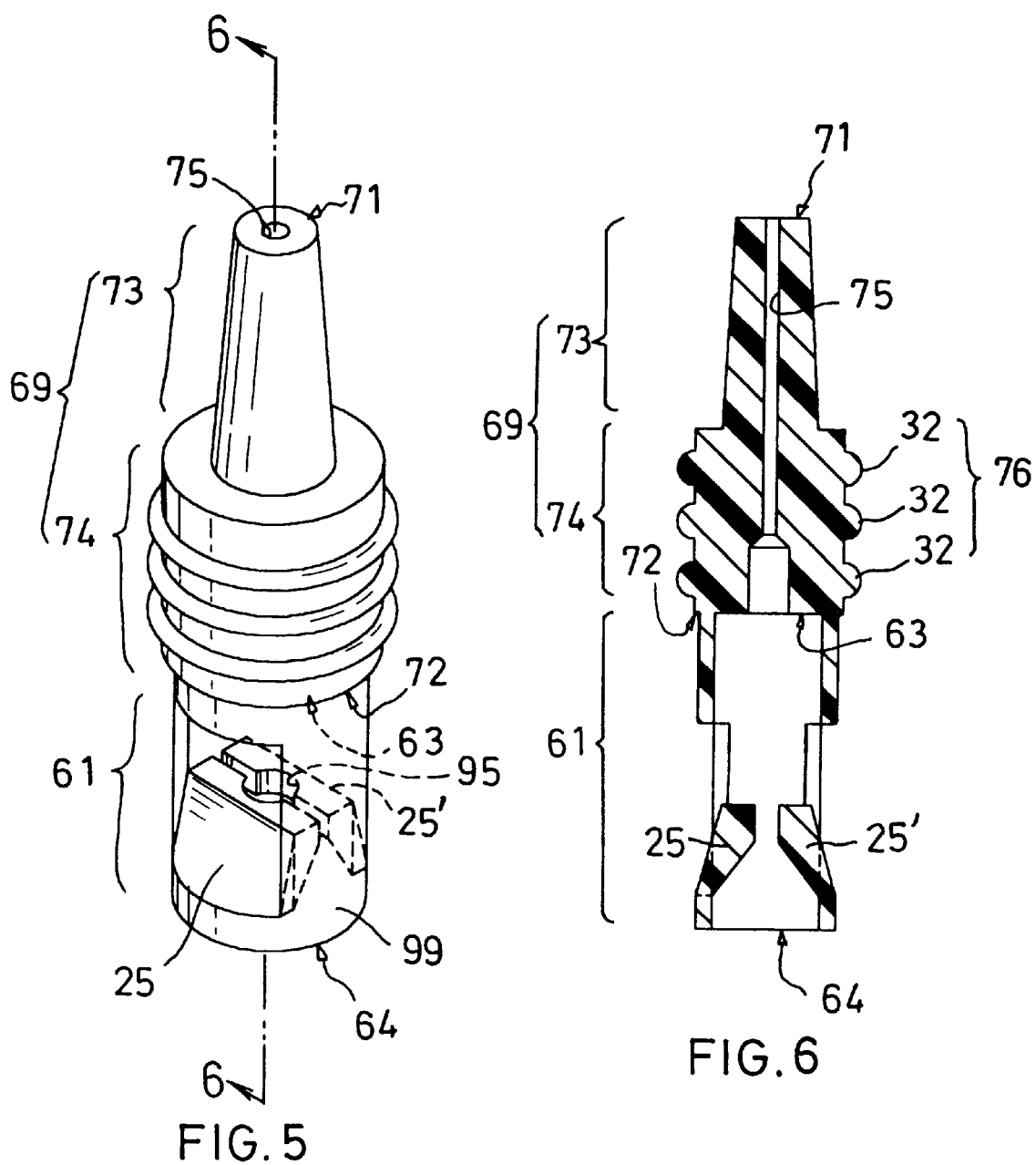

SAFETY SYRINGE WITH RETRACTABLE STANDARD NEEDLES

BACKGROUND OF THE INVENTION

1. Field of the Invention

The present invention relates to a safety syringe in which the injection needle can be pulled back into the syringe barrel after injection.

2. Description of the Prior Art

Various types of disposable syringes are widely used nowadays. After discarded, large amount of such syringes result in problem of pollution of environment. The used syringes often impale medical personnel and infect the personnel with viruses or bacteria carried by the patients. Especially, in case the medical personnel are infected with AIDS virus, the personnel may die innocently.

In order to solve these problems, various types of retractable syringes have been developed. For example, a spring is installed between the syringe barrel and the piston for pulling the needle back into the barrel after injection. However, due to the property of the liquid medicine, the material of the spring is strictly limited. Therefore, the structure of such syringe is complicated and the manufacturing cost is very high.

Various types of safety syringes free from the springs have been also developed. In such syringe, a latch member is disposed at the bottom of the barrel, whereby when the plunger is pushed to the bottom of the barrel, the latch member latches the plunger with the needle. Therefore, when the plunger is pulled back, the needle is retracted into the barrel along with the plunger so as to avoid impalement of the medical personnel or other persons.

In order to avoid leakage of the liquid medicine and unexpected dropping of the needle from the barrel, the needle must be firmly assembled with the barrel. However, in the case that the needle is excessively firmly assembled with the barrel, it will be difficult to pull the needle back into the barrel. Therefore, it is troublesome to consider both situations.

In the applicant's U.S. Pat. No. 5,899,887, a replaceable needle structure is provided. Therefore, the manufacturers are unnecessary to manufacture and prepare safety syringes with many different kinds of needles.

SUMMARY OF THE INVENTION

In order to solve the above problems, it is a primary object of the present invention to provide a safety syringe with retractable standard needle employing a standard needle holder which can be more firmly mounted on the syringe barrel.

It is a further object of the present invention to provide a safety syringe with retractable standard needle which has simplified structure and can be more easily manufactured and used. The structure prevents two sets of needle pulling members from being latched with each other accidentally.

It is still a further object of the present invention to provide a safety syringe with retractable standard needle in which the plunger can be easily aligned with the injection needle and easily and firmly latched with the injection needle so that the injection needle can be reliably pulled into the syringe barrel.

According to the above objects, the safety syringe with retractable standard needle of the present invention includes: a syringe barrel having a first end, a second end and a first axis, near the first end of the syringe barrel being disposed a needle socket, near the second end of the syringe barrel being disposed a barrel section, the barrel section being formed with an internal chamber surrounding the first axis, the needle socket having a needle holder cavity surrounding the first axis, an annular shoulder section being formed between the internal chamber and the needle holder cavity, the internal chamber having a first end and a second end, the second end of the internal chamber being formed with a first opening coinciding with the second end of the syringe barrel, the first end of the internal chamber communicating with the needle holder cavity, the outer circumference of the first opening being formed with an annular stopper section, the inner wall of the first end of the internal chamber being formed with at least one entrance recess axially extending along the internal chamber, the first end of the syringe barrel being formed with a second opening cutting off the annular stopper section to form stopper edge, the distance between the edge of the second opening and the first axis being defined as a first width; a plunger having a first end and a second end, the first end being disposed with a piston and is rotatably fitted in the syringe barrel, the plunger having a second axis, the second end of the plunger having at least one stopper section, the distance between the outer edge of the stopper section and the second axis of the plunger being defined as a second width, the second width being larger than the radius of the internal chamber but smaller than the first width, whereby the stopper section of the plunger is stopped by the stopper edge of the syringe barrel and thus the piston of the first end of the plunger cannot touch the annular shoulder section between the internal chamber and the needle holder cavity, when the plunger is rotated to align the stopper section thereof with the second opening of the first end of the syringe barrel, the stopper section of the plunger being slided from the second opening into the entrance recess of the internal chamber, at this time, the piston at the first end of the plunger being permitted to touch the annular shoulder section between the internal chamber and the needle holder cavity; a first needle holder having a first end and a second end, the second end having a fitting section; an injection needle inserted in the first end of the first needle holder; a second needle holder having a first end, a second end, a second fitting section and a plug section, the second fitting section being formed at the first end and being detachably fitted with the first fitting section of the first needle holder, the plug section being formed at the second end and being fitted in the needle holder cavity of the needle socket of the syringe barrel, the second needle holder having a third axis and being formed with a through hole passing through the third axis for guiding the liquid to flow from the syringe barrel through the through hole to the injection needle or from the injection needle through the through hole to the syringe barrel; and a needle pulling mechanism including: a first needle pulling member having a first end and a second end, the first end being connected with one of the first end of the plunger and the second end of the second needle holder, the first needle pulling member having at least one click, each click having a first end and a second end, the first end being resiliently movably connected with the second end of the first needle pulling member, the distance between the first end of the click and either of the second axis and the first axis being defined as a first distance, the second end of the click extending toward the second end of the first needle pulling member, in a free state, the distance between the second end of the click and either of the second axis and the first axis being defined as a second distance, the second distance being smaller than the first distance, the distance between the second end of the click and the first end of the first needle pulling member being defined as a third distance, the distance between the first end of the click and the first end of the first needle pulling member being defined as a fourth distance, the third distance being smaller than the fourth distance, whereby the click serves as a reverse thorn; and a second needle pulling member having a first end and a second end, the first end being connected with other of the first end of the plunger and the second end of the second needle holder, the first end of the second needle pulling member being formed as a neck stem, the second end of the second needle pulling member being formed as a detent having a hook section, the hook section having a radially extending hook face, when the first end of the plunger being pushed to the first end of the syringe barrel, the hook section of the detent stretching open and slides over the second end of the click, when the plunger is pulled from the first end of the syringe barrel to the second end thereof, the hook face of the hook section of the detent abutting against the second end of the click and forces the second end of the click to firmly clamp the neck stem and abut against the hook face of the hook section of the detent, at this time, the first and second needle holders and the injection needle being together pulled into the syringe barrel.

The safety syringe with retractable standard needle of the present invention further includes at least two clicks which are radially arranged about the axis.

The safety syringe with retractable standard needle of the present invention, wherein the clicks are alternatively integrally connected, at least a slit being formed with at least an adjoining portions of the clicks a passing hole being formed with the adjoining portions of the slits, the hook section of the detent being cable of stretching open the slits and the passing hole and smoothly slide over the passing hole, and the hook face of the hook section abuting against the second end of the click and forcing the second end of the click to firmly clamp the neck stem and abut against the hook face of the hook section of the detent.

In the safety syringe with retractable standard needle of the present invention, the second end of the internal chamber further has at least two opposite first latch sections extending toward the center of the internal chamber, the distance between the edges of the two first latch sections being defined as a third width, the second end of the internal chamber further having at least two notched sections formed between the two first latch sections, the distance between at least two opposite edges of the notched sections being defined as a fourth width.

In the safety syringe with retractable standard needle of the present invention the second end of the first needle holder further has at least two opposite second latch sections which respectively radially outward extend, the distance between the edges of the second latch sections being defined as a fifth width which is between the third width and the fourth width, the second latch sections axially extending from the notched sections into the internal chamber, by means of rotating the first needle holder, the first needle holder being engaged and latched with the second end of the internal chamber.

In the safety syringe with retractable standard needle of the present invention, the first needle holder is a commonly used standard needle holder and the first fitting section thereof is an inner truncated conic hole.

In the safety syringe with retractable standard needle of the present invention, the second fitting section is a truncated cone which can be fitted into the inner truncated conic hole of the first fitting section or separated therefrom.

The safety syringe with retractable standard needle of the present invention further includes a leakproof structure. The leakproof structure includes at least one sealing fixing ring which is integrally formed on outer wall of the plug section of the second needle holder to tightly contact with the inner wall of the needle holder cavity.

BRIEF DESCRIPTION OF THE DRAWINGS

FIG. 3 i s a sectional view taken along line 3—3 of FIG. 2;

FIG. 4 is a sectional view take n along line 4—4 of FIG. 3;

FIG. 5 is a perspective view of the first needle holder of the present invention;

FIG. 6 is a sectional view taken along line 6—6 of FIG. 5;

DETAILED DESCRIPTION OF THE PREFERRED EMBODIMENTS

Figure 1:
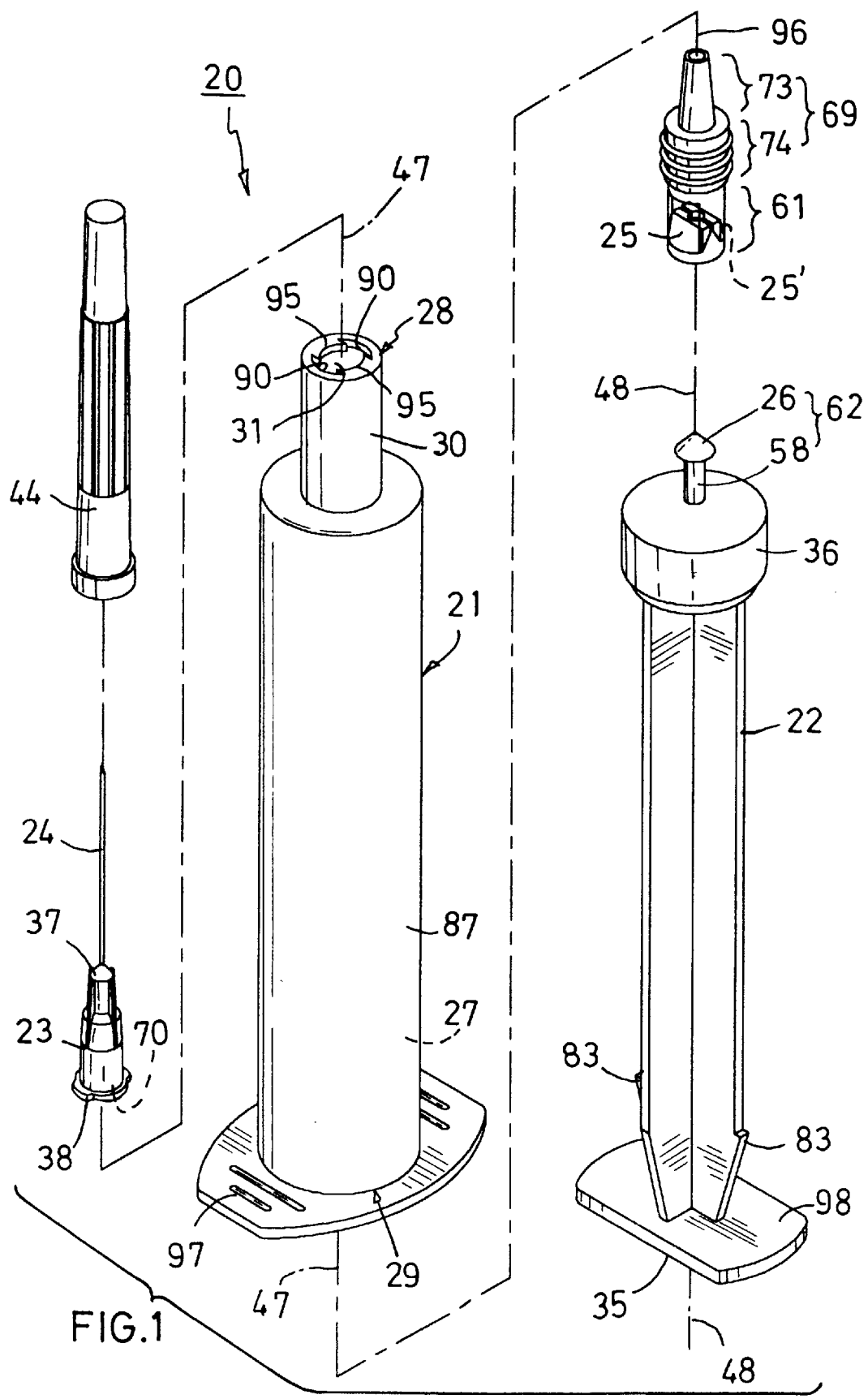
FIG. 1 is a perspective exploded view of a first embodiment of the present invention.
Figure 2:
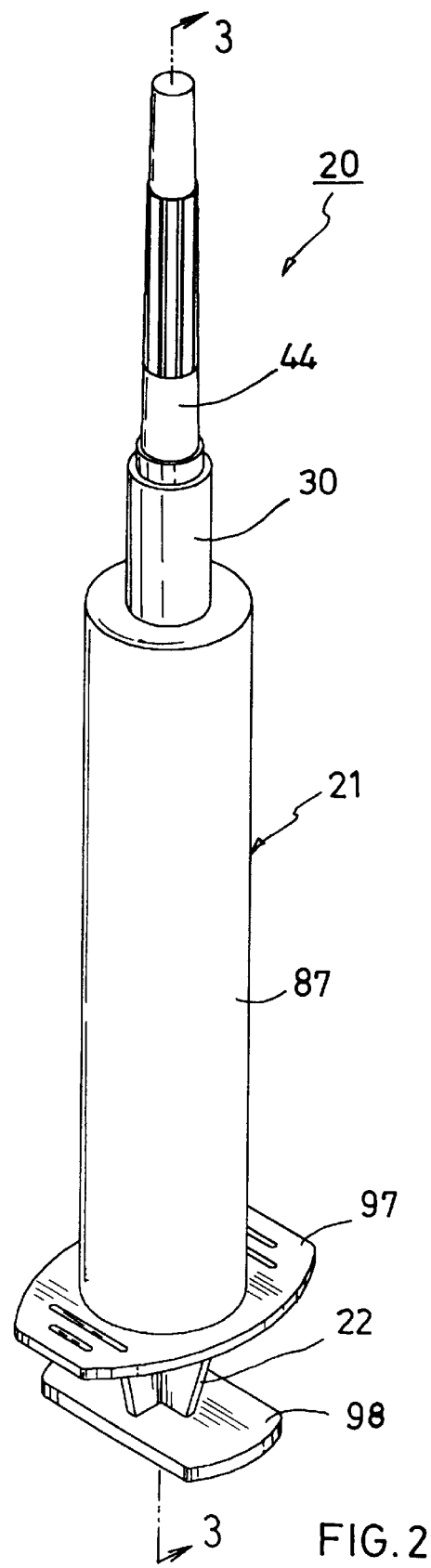
FIG. 2 is a perspective assembled view of the first embodiment of the present invention.
Figure 7:
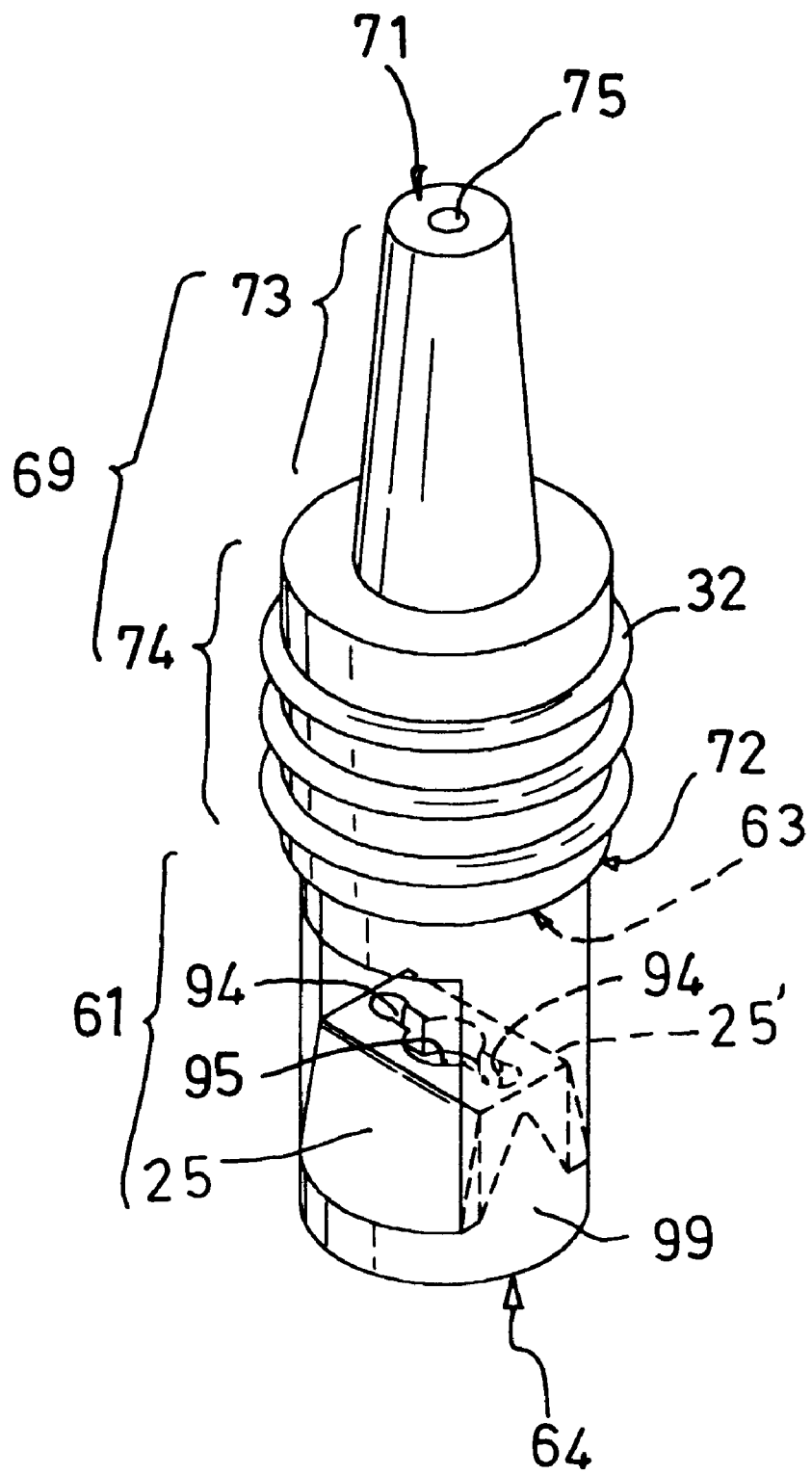
FIG. 7 is a perspective view another embodiment of the first needle pulling member of the present invention.
Figures 8, 9:
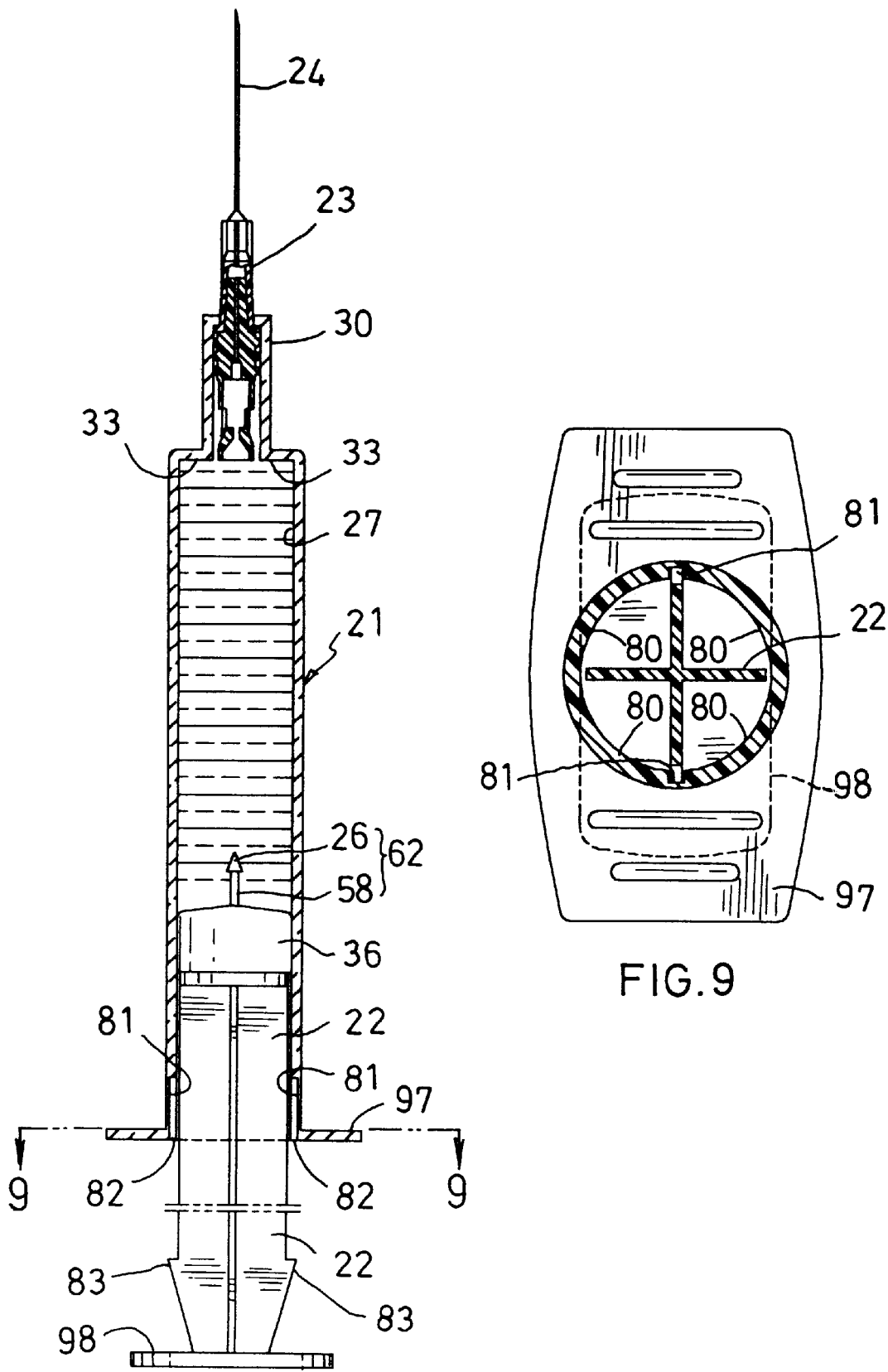
FIG. 8 is a sectional view showing that the liquid medicine has been sucked into the syringe barrel of the first embodiment of the present invention.
FIG. 9 is a sectional view taken along line 9—9 of FIG. 8.
Figure 10:
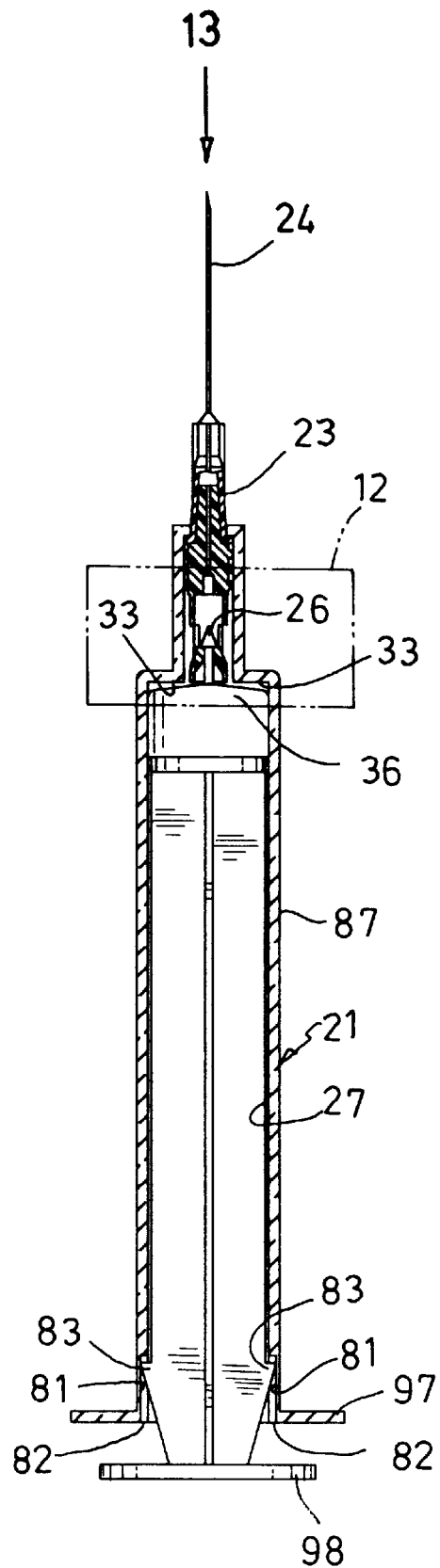
FIG. 10 is a sectional view showing that the liquid medicine is completely injected and the detent of the plunger is hooked with the click of the needle holder of the first embodiment.
Figure 11:
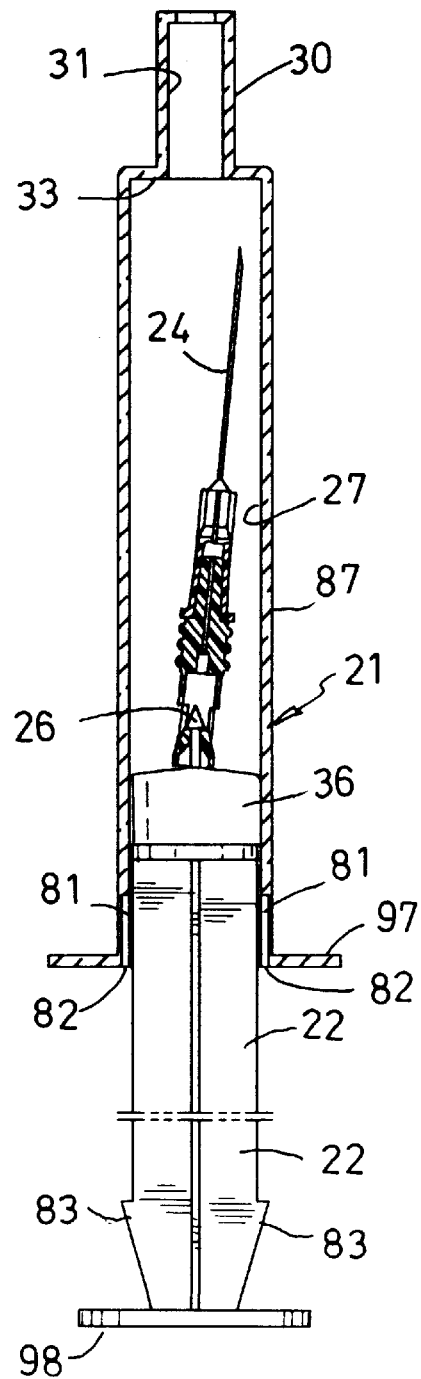
FIG. 11 is a sectional view of the first embodiment, showing that the first and second needle holders and the injection needle are all pulled into the syringe barrel and the injection needle tilts toward the inner wall of the syringe barrel.
Figure 12:
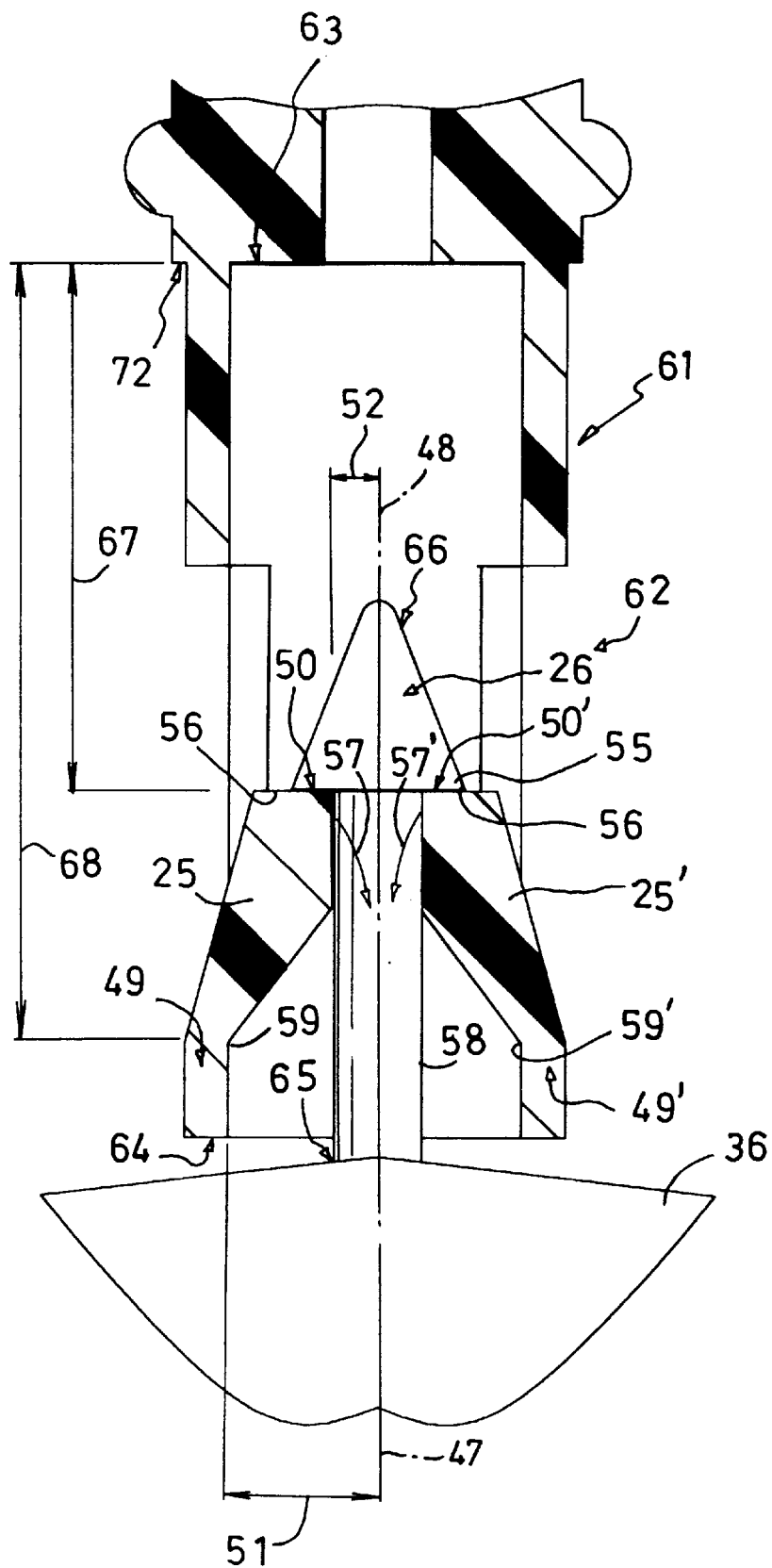
FIG. 12 is an enlarged sectional view of area 12 circled by phantom line in FIG. 10, showing that the plunger is pulled downward and the two clicks are forced toward the plunger to clamp the same and the detent is passed through the clicks and clamped by the clicks.
Figure 13:
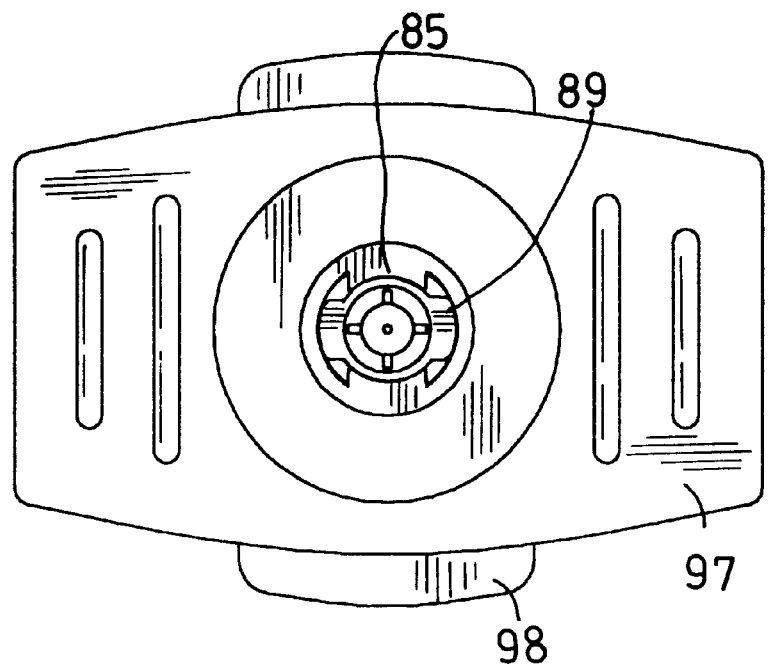
FIG. 13 is a top view seen in a direction of arrow 13 of FIG. 10, showing that the injection needle has not been installed well yet.
Figure 14:
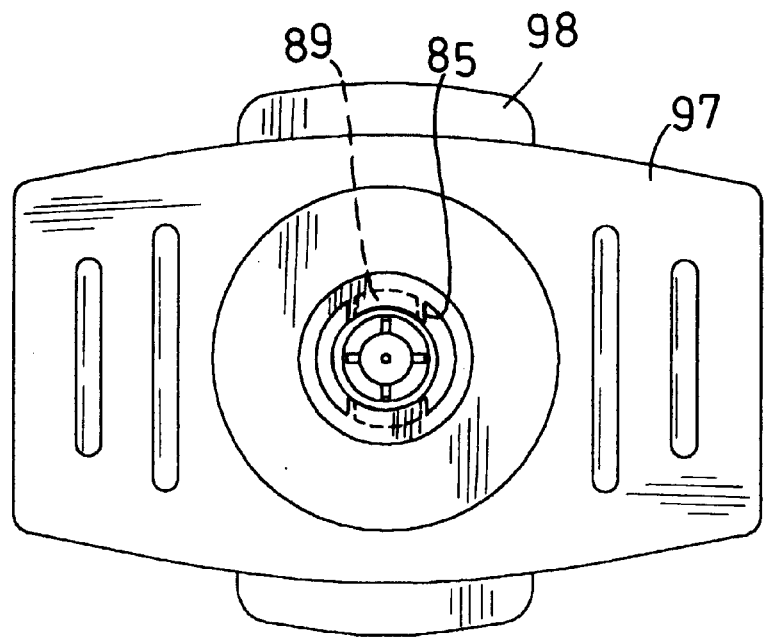
FIG. 14 is a top view seen in a direction of arrow 13 of FIG. 10, showing that the injection needle has been installed well.
Figure 15:
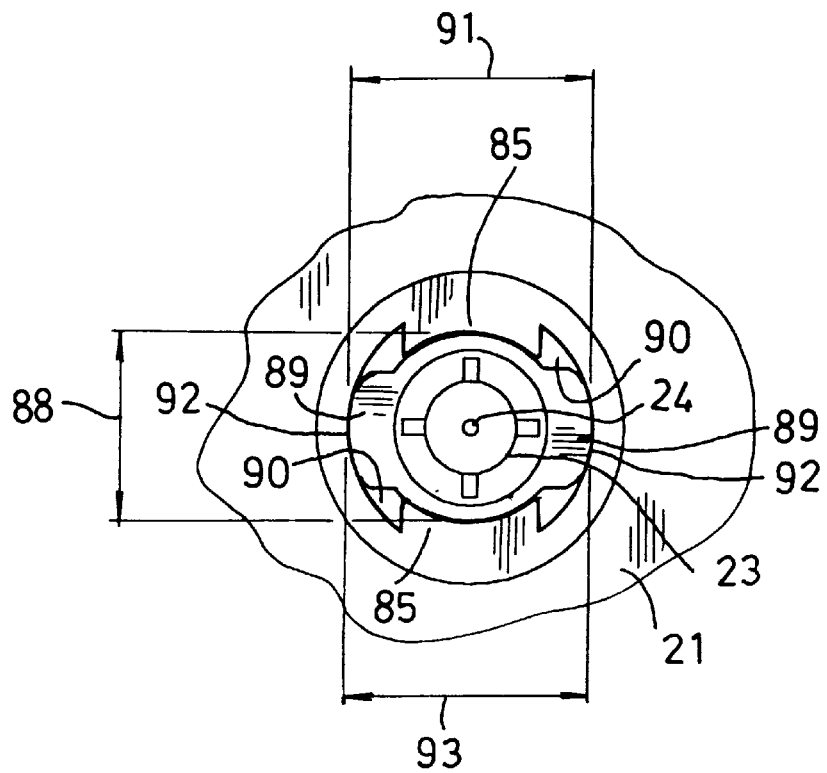
FIG. 15 is an enlarged view of the central area of FIG. 13.
Figure 16:
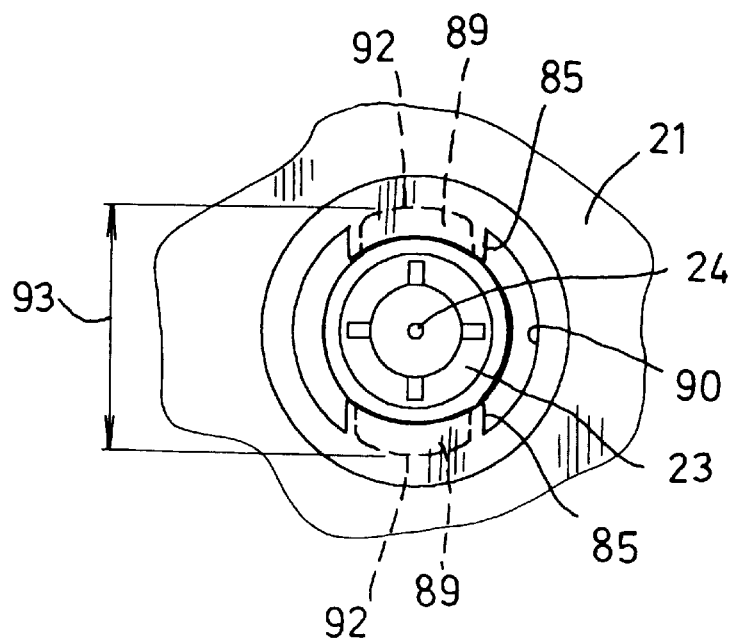
FIG. 16 is an enlarged view of the central area of FIG. 14.

Please refer to FIGS. 1 to 16. The safety syringe 20 of the present invention includes a syringe barrel 21, a plunger 22, a first needle holder 23, a second needle holder 69 and an injection needle 24.

The syringe barrel 21 has a first end 28, a second end 29 and a first axis 47. Near the first end 28 of the syringe barrel 21 is disposed a needle socket 30. Near the second end 29 of the syringe barrel 21 is disposed a barrel section 87. The barrel section 87 is formed with an internal chamber 27 surrounding the first axis 47. The needle socket 30 has a needle holder cavity 31 surrounding the first axis 47. An annular shoulder section 33 is formed between the internal chamber 27 and the needle holder cavity 31. The internal chamber 27 has a first end 77 and a second end 78. The second end 78 of the internal chamber 27 is formed with a first opening 79 coinciding with the second end 29 of the syringe barrel 21. The first end 77 of the internal chamber 27 communicates with the needle holder cavity 31. The outer circumference of the first opening 79 is formed with an annular stopper section. The inner wall of the first end 77 of the internal chamber 27 is formed with at least one entrance recess 81 axially extending along the internal chamber 27. The second end 29 of the syringe barrel 21 is formed with a second opening 82 cutting off the annular stopper section to form stopper edge 80. The distance between the edge of the second opening 82 and the first axis 47 is defined as a first width 84. The second end 29 of the syringe barrel 21 has a transversely extending flange 97 for a user's finger to hook.

The plunger 22 has a first end 34 and a second end 35. The first end 34 is disposed with a piston 36 and is rotatably fitted in the syringe barrel 21. The plunger 22 has a second axis 48. The second end 35 of the plunger 22 has at least one stopper section 83. The distance between the outer edge of the stopper section 83 and the second axis 48 of the plunger 22 is defined as a second width 86. The second width 86 is larger than the radius R of the internal chamber 27 but smaller than the first width 84, whereby the stopper section 83 of the plunger 22 is stopped by the stopper edge 80 of the syringe barrel 21 and thus the piston 36 of the first end 34 of the plunger 22 cannot touch the annular shoulder section 33 between the internal chamber 27 and the needle holder cavity 31. When the plunger 22 is rotated to align the stopper section 83 thereof with the second opening 82 of the first end 28 of the syringe barrel 21, the stopper section 83 of the plunger 22 can be slided from the second opening 82 into the entrance recess 81 of the internal chamber 27. At this time, the piston 36 at the first end 34 of the plunger 22 is permitted to touch the annular shoulder section 33 between the internal chamber 27 and the needle holder cavity 31. The second end of the plunger 22 has a transversely extending flange 98 for a user's finger to push and press.

The first needle holder 23 has a first end 37 and a second end 38. The second end 38 has a fitting section 70. The injection needle 24 is inserted in the first end 37 of the first needle holder 23. A needle sheath 44 is fitted a round t he first needle holder 23 for preventing the injection needle 24 from being contaminated 24 and avoiding impalement of a user by the injection needle 24.

The second needle holder 69 has a first end 71, a second end 72, a second fitting section 73 and a plug section 74. The second fitting section 73 is formed at the first end 71 and is detachably fitted with the first fitting section 70 of the first needle holder 23. The plug section 74 is formed at the second end 72 and is fitted in the needle holder cavity 31 of the needle socket 30 of the syringe barrel 21. The second needle holder 69 has a third axis 96 and is formed with a through hole 75 passing through the third axis 96 for guiding the liquid to flow from the syringe barrel 21 through the through hole 75 to the injection needle 24 or from the injection needle 24 through the through hole 75 to the syringe barrel 21.

The needle pulling mechanism includes a first needle pulling member 61 having a first end 63 and a second end 64. The first end 63 is connected with one of the first end 34 of the plunger 22 and the second end 72 of the second needle holder 69. The first needle pulling member 61 has at least one click 25. Each click 25, 25' has a first end 49, 49' and a second end 50, 50'. The first end 49, 49' is integrally connected with the sleeve 99, whereby the click 25, 25' is resiliently movably connected with the second end 64 of the first needle pulling member 61. In addition, the distance between the first end 49, 49' of the click 25, 25' and either of the second axis 48 and the first axis 47 is defined as a first distance 51. The second end 50, 50' of the click 25, 25' extends toward the second end 64 of the first needle pulling member 61. In a free state, the distance between the second end 50, 50' of the click 25, 25' and either of the second axis 48 and the first axis 47 is defined as a second distance. The second distance 52 is smaller than the first distance 51. The distance between the second end 50, 50' of the click 25, 25' and the first end 63 of the first needle pulling member 61 is defined as a third distance 67. The distance between the first end 49, 49' of the click 25, 25' and the first end 63 of the first needle pulling member 61 is defined as a fourth distance 68. The third distance is smaller than the fourth distance 68, whereby the click 25, 25' serves as a reverse thorn.

The second needle pulling member 62 has a first end 65 and a second end 66. The first end 65 is connected with the other of the first end 34 of the plunger 22 and the second end of the second needle holder 69. The first end 65 of the second needle pulling member 62 is formed as a neck stem. The second end 66 of the second needle pulling member 62 is formed as a detent 26 having a hook section 55. The hook section 55 has a radially extending hook face 56. When the first end 34 of the plunger 22 is pushed to the first end 28 of the syringe barrel 21, the hook section 55 of the detent 26 stretches open the click and slides over the second end 50, 50' of the click 25, 25'. When the plunger 22 is pulled from the first end 28 of the syringe barrel 21 to the second end 29 thereof, the hook face 56 of the hook section 55 of the detent 26 abuts against the second end 50, 50' of the click 25, 25' and forces the second end 50, 50' of the click 25, 25' to firmly clamp the neck stem 58 and abut against the hook face 56 of the hook section 55 of the detent 26. At this time, the first and second needle holders 23, 69 and the injection needle 24 are together pulled into the syringe barrel 21. Preferably, there are at least two clicks 25, 25' which are radially arranged about the axis.

The above clicks 25, 25' can be alternatively integrally connected. The adjoining portions of the clicks 25, 25' can be formed with one or more slits 94. The adjoining portions of the slits 94 and the first axis 47 is formed with a passing hole 95, whereby the hook section 55 of the detent 26 can stretch open the slits 94 and the passing hole 95 and smoothly slide over the passing hole 95. At this time, the hook face 56 of the hook section 55 abuts against the second end 50, 50' of the click 25, 25' and forces the second end 50, 50' of the click 25, 25' to firmly clamp the neck stem 58 and abut against the hook face 56 of the hook section 55 of the detent 26. Under such circumstance, the first and second needle holders 23, 69 and the injection needle 24 are together pulled into the syringe barrel 21.

The first end 28 of the internal chamber 27 further has at least two opposite first latch sections 85 extending toward the center of the internal chamber 27. The distance between the edges of the two first latch sections 85 is defined as a third width 88. The first end 28 of the internal chamber 27 further has at least two notched sections 90 formed between the two first latch sections 85. The distance between at least two opposite edges of the notched sections 90 is defined as a fourth width 91.

The second end 38 of the first needle holder 23 further has at least two opposite second latch sections 89 which respectively radially outward extend. The distance between the edges 92 of the second latch sections 89 is defined as a fifth width 93 which is between the third width 88 and the fourth width 91. The second latch sections 89 axially extend from the notched sections 90 into the internal chamber 27. By means of rotating the first needle holder 23, the first needle holder 23 can be engaged and latched with the second end 78 of the internal chamber 27.

The first needle holder 23 is a commonly used standard needle holder. The first fitting section 70 thereof is an inner truncated conic hole. The second fitting section 73 is a truncated cone which can be fitted into the inner truncated conic hole of the first fitting section 70 or separated therefrom.

The safety syringe of the present invention further includes a leakproof structure 76. The leakproof structure 76 includes at least one sealing fixing ring 32 which is integrally formed on outer wall of the plug section of the second needle holder 69 to tightly contact with the inner wall of the needle holder cavity 31.

When assembled in a manufacturing factory, the plunger 22 is inserted into the internal chamber 27 of the syringe barrel 21 with the stopper section 83 of the plunger 22 stopped by the stopper edge 80 of the syringe barrel 21. At this time, the piston 36 at the first end 34 of the plunger 22 cannot touch the annular shoulder section 33 between the internal chamber 27 and the needle holder cavity 31. Therefore, the hook section 55 of the plunger 22 is prevented from being latched with the clicks 25, 25' by accident.

A user chooses a necessary injection needle 24 and the second latch sections 89 of the first needle holder 23 are axially fitted from the notched sections 90 of the second end 29 of the internal chamber 27 into the internal chamber 27. By means of rotating the first needle holder 23, the first needle holder 23 is latched with the second end 78 of the internal chamber 27 to complete the assembly of the injection needle.

After a liquid medicine is sucked into the syringe barrel 21, the plunger 22 is rotated by about 90 degrees so as to align the stopper section 83 thereof with the second opening 82 of the first end 28 of the syringe barrel 21. Thereafter, the injection can be started. When injected, the stopper section 83 of the plunger 22 can be slided from the second opening 82 into the entrance recess 81 of the internal chamber 27. At this time, the piston 36 of the first end 34 of the plunger 22 is permitted to be pushed to the annular shoulder section 33 of the syringe barrel 21. When the piston 36 is pushed to the annular shoulder section 33 between the internal chamber 27 and the needle holder cavity 31, the hook section 55 of the detent 26 stretches open and slides over the second ends 50, 50' of the clicks 25, 25'. When the plunger 22 is pulled from the first end 28 of the syringe barrel 21 to the second end 29 thereof, the hook face 56 of the hook section 55 of the detent 26 abuts against the second end 50, 50' of the click 25, 25' and forces the second end 50, 50' of the click 25, 25' to move toward each other in the direction of arrows 57, 57' and thus firmly clamp the neck stem 58 and abut against the hook face 56 of the hook section 55 of the detent 26. At this time, the first and second needle holders 23, 69 and the injection needle 24 can be together pulled into the syringe barrel 21.

According to the above arrangements, the present invention has the following advantages:

1. The safety syringe of the present invention employs commonly used standard needle holder so that a user can freely conveniently replace the needle with another kind of needle as necessary to meet the requirement of different injection. In addition, once the injection needle is installed, the injection needle is firmly latched with the latch section without unexpected detachment.

2. In the safety syringe of the present invention, by means of the stopper edge 80 and entrance recess 81 of the second end 29 of the syringe barrel 21 and cooperative stopper section 83 of the second end 35 of the plunger 22, the hook section 55 of the plunger 22 is prevented from being accidentally latched with the clicks 25, 25'.

3. The safety syringe of the present invention is able to avoid leakage of the liquid medicine and prevent the injection needle from unexpectedly detaching from the syringe barrel. As well, the safety syringe of the present invention enables a user to easily pull the injection needle into the syringe barrel.

4. The safety syringe of the present invention enables the plunger to be easily and firmly latched with the injection needle so that the injection needle can be reliably pulled into the syringe barrel.

It is to be understood that the above description and drawings are only used for illustrating some embodiments of the present invention, not intended to limit the scope thereof. Any variation and derivation from the above description and drawings should be included in the scope of the present invention.

What is claimed is:

1. Safety syringe with retractable standard needle, comprising:

(A) a syringe barrel having a first end, a second end and a first axis, near the first end of the syringe barrel being disposed a needle socket, near the second end of the syringe barrel being disposed a barrel section, the barrel section being formed with an internal chamber surrounding the first axis, the needle socket having a needle holder cavity surrounding the first axis, an annular shoulder section being formed between the internal chamber and the needle holder cavity, the internal chamber having a first end and a second end, the second end of the internal chamber being formed with a first opening coinciding with the second end of the syringe barrel, the first end of the internal chamber communicating with the needle holder cavity, the outer circumference of the first opening being formed with an annular stopper section, the first end of the internal chamber having an inner wall formed with at least one entrance recess axially extending along the internal chamber, the second end of the syringe barrel being formed with a second opening cutting off the annular stopper section to form stopper edge, the distance between the edge of the second opening and the first axis being defined as a first width;

(B) a plunger having a first end and a second end, the first end being disposed with a piston and is rotatably fitted in the syringe barrel, the plunger having a second axis, the second end of the plunger having at least one stopper section, the distance between an outer edge of the stopper section and the second axis of the plunger being defined as a second width, the second width being larger than the radius of the internal chamber but smaller than the first width, whereby the stopper section of the plunger is stopped by the stopper edge of the syringe barrel and thus the piston of the first end of the plunger cannot touch the annular shoulder section between the internal chamber and the needle holder cavity, when the plunger is rotated to align the stopper section thereof with the second opening of the first end of the syringe barrel, the stopper section of the plunger being slid from the second opening into the entrance recess of the internal chamber, at this time, the piston at the first end of the plunger being permitted to touch the annular shoulder section between the internal chamber and the needle holder cavity;

(C) a first needle holder having a first end and a second end, the second end having a first fitting section;

(D) an injection needle inserted in the first end of the first needle holder;

(E) a second needle holder having a first end, a second end, a second fitting section and a plug section, the second fitting section being formed at the first end and being detachably fitted with the first fitting section of the first needle holder, the plug section being formed at the second end and being fitted in the needle holder cavity of the needle socket of the syringe barrel, the second needle holder having a third axis and being formed with a through hole passing through the third axis for guiding the liquid to flow from the syringe barrel through the through hole to the injection needle or from the injection needle through the through hole to the syringe barrel; and (F) a needle pulling mechanism including:
(a) a first needle pulling member having a first end and a second end, the first end being connected with one of the first end of the plunger and the second end of the second needle holder, the first needle pulling member having at least one click, each click having a first end and a second end, the first end being resiliently movably connected with the second end of the first needle pulling member, the distance between the first end of the click and either of the second axis and the first axis being defined as a first distance, the second end of the click extending toward the second end of the first needle pulling member, in a free state, the distance between the second end of the click and either of the second axis and the first axis being defined as a second distance, the second distance being smaller than the first distance, the distance between the second end of the click and the first end of the first needle pulling member being defined as a third distance, the distance between the first end of the click and the first end of the first needle pulling member being defined as a fourth distance, the third distance being smaller than the fourth distance, whereby the click serves as a reverse thorn; and
(b) a second needle pulling member having a first end and a second end, the first end being connected with the other of the first end of the plunger and the second end of the second needle holder, the first end of the second needle pulling member being formed as a neck stem, the second end of the second needle pulling member being formed as a detent having a hook section, the hook section having a radially extending hook face, when the first end of the plunger being pushed to the first end of the syringe barrel, the hook section of the detent displacing and sliding over the second end of the click, when the plunger is pulled from the first end of the syringe barrel to the second end thereof, the hook face of the hook section of the detent abutting against the second end of the click and forces the second end of the click to firmly clamp the neck stem and abut against the hook face of the hook section of the detent, at this time, the first and second needle holders and the injection needle being together pulled into the syringe barrel.

2. The safety syringe with retractable standard needle as claimed in claim 1, wherein the safety syringe includes at least two clicks which are radially arranged about the axis of the second needle holder.

3. The safety syringe with retractable standard needle as claimed in claim 1, wherein the clicks are alternatively integrally connected, at least a slit being formed with at least an adjoining portions of the clicks, a passing hole being formed with the adjoining portions of the slits, the hook section of the detent being cable of stretching open the slits and the passing hole and smoothly slide over the passing hole, and the hook face of the hook section abutting against the second end of the click and forcing the second end of the click to firmly clamp the neck stem and abut against the hook face of the hook section of the detent.

4. The safety syringe with retractable standard needle as claimed in claim 1, wherein the first end of the internal chamber further has at least two opposite first latch sections extending toward the center of the internal chamber, the distance between the edges of the two first latch sections being defined as a third width, the first end of the internal chamber further having at least two notched sections formed between the two first latch sections, the distance between the at least two opposite edges of the notched sections being defined as a fourth width.

5. The safety syringe with retractable standard needle as claimed in claim 4, wherein the first end of the first needle holder further has at least two opposite second latch sections which respectively radially outward extend, a distance between opposing edges of the second latch sections being defined as a fifth width which is between the third width and the fourth width, the second latch sections axially extending from the notched sections into the internal chamber, by means of rotating the first needle holder, the first needle holder being engaged and latched with the first end of the internal chamber.

6. The safety syringe with retractable standard needle as claimed in claim 1, wherein the first needle holder is a commonly used standard needle holder and the first fitting section thereof is an inner truncated conic hole.

7. The safety syringe with retractable standard needle as claimed in claim 6, wherein the second fitting section is a truncated cone which can be fitted into the inner truncated conic hole of the first fitting section or separated therefrom.

8. The safety syringe with retractable standard needle as claimed in claim 1, further comprising a leakproof structure, the leakproof structure including at least one sealing fixing ring which is integrally formed on an outer wall of the plug section of the second needle holder to tightly contact with an inner wall of the needle holder cavity.

9. Safety syringe with retractable standard needle, comprising:
(A) a syringe barrel having a first end, a second end and a first axis, near the first end of the syringe barrel being disposed a needle socket, near the second end of the syringe barrel being disposed a barrel section, the barrel section being formed with an internal chamber surrounding the second axis, the needle socket having a needle holder cavity surrounding the first axis, an annular shoulder section being formed between the internal chamber and the needle holder cavity, the internal chamber having a first end and a second end, the second end of the internal chamber being formed with a first opening coinciding with the second end of the syringe barrel, the first end of the internal chamber communicating with the needle holder cavity, the outer circumference of the first opening being formed with an annular stopper section, an inner wall of the first end of the internal chamber being formed with at least one entrance recess axially extending along the internal chamber, the second end of the syringe barrel being formed with a second opening cutting off the annular stopper section to form stopper edge, the distance between the edge of the second opening and the first axis being defined as a first width; and (B) a plunger having a first end and a second end, the first end being disposed with a piston and is rotatably fitted in the syringe barrel, the plunger having a second axis, the second end of the plunger having at least one stopper section, the distance between the outer edge of the stopper section and the second axis of the plunger being defined as a second width, the second width being larger than the radius of the internal chamber but smaller than the first width, whereby the stopper section of the plunger is stopped by the stopper edge of the syringe barrel and thus the piston of the first end of the plunger cannot touch the annular shoulder section between the internal chamber and the needle holder cavity, when the plunger is rotated to align the stopper section thereof with the second opening of the first end of the syringe barrel, the stopper section of the plunger being slided from the second opening into the entrance recess of the internal chamber, at this time, the piston at the first end of the plunger being permitted to touch the annular shoulder section between the internal chamber and the needle holder cavity.

10. The safety syringe with retractable standard needle as claimed in claim 9, further comprising:

(a) a first needle holder having a first end and a second end, the second end having a fitting section;

(b) an injection needle inserted in the first end of the first needle holder; and (c) a second needle holder having a first end, a second end, a second fitting section and a plug section, the second fitting section being formed at the first end and being detachably fitted with the first fitting section of the first needle holder, the plug section being formed at the second end and being fitted in the needle holder cavity of the needle socket of the syringe barrel, the second needle holder having a third axis and being formed with a through hole passing through the third axis for guiding the liquid to flow from the syringe barrel through the through hole to the injection needle or from the injection needle through the through hole to the syringe barrel.

11. The safety syringe with retractable standard needle as claimed in claim 10, wherein the first end of the internal chamber further has at least two opposite first latch sections extending toward the center of the internal chamber, a distance between edges of the two first latch sections being defined as a third width, the first end of the internal chamber further having at least two notched sections formed between the two first latch sections, the distance between at least two opposite edges of the notched sections being defined as a fourth width.

12. The safety syringe with retractable standard needle as claimed in claim 11, wherein the second end of the first needle holder further has at least two opposite second latch sections which respectively radially outward extend, a distance between edges of the second latch sections being defined as a fifth width which is between the third width and the fourth width, the second latch sections axially extending from the notched sections into the internal chamber, by means of rotating the first needle holder, the first needle holder being engaged and latched with the second end of the internal chamber.

* * * * *